United States Patent [19]
Garry et al.

[11] Patent Number: 5,834,215
[45] Date of Patent: *Nov. 10, 1998

[54] METHOD FOR DETECTING ANTIPOLYMER ANTIBODIES AND DIAGNOSING SILICONE RELATED DISEASE (SRD) FIBROMYALGIA AND CHRONIC FATIGUE SYNDROME (CFS)

[75] Inventors: Robert F. Garry; Scott A. Tenenbaum; Douglas R. Plymale, all of New Orleans, La.

[73] Assignee: The Administrators of the Tulane Educational Fund, New Orleans, La.

[ * ] Notice: The term of this patent shall not extend beyond the expiration date of Pat. No. 5,620,859.

[21] Appl. No.: 546,333

[22] Filed: Oct. 20, 1995

Related U.S. Application Data

[63] Continuation-in-part of Ser. No. 320,889, Oct. 5, 1994, Pat. No. 5,620,859.

[51] Int. Cl.$^6$ .......................... G01N 33/53; G01N 33/564
[52] U.S. Cl. .......................... 435/7.9; 435/7.1; 435/7.92; 435/7.94; 435/795; 435/975; 436/501; 436/506; 436/509; 436/518; 436/72; 436/811
[58] Field of Search .......................... 435/7.1, 7.9, 7.92, 435/7.93, 7.94, 7.95, 968, 975; 436/501, 506, 509, 518, 528, 531, 93, 811

[56] References Cited

U.S. PATENT DOCUMENTS

| | | |
|---|---|---|
| 4,918,165 | 4/1990 | Soll et al. . |
| 5,312,620 | 5/1994 | Ribi ........................ 424/78.31 |
| 5,338,661 | 8/1994 | Jensenius et al. . |
| 5,340,720 | 8/1994 | Stetler ........................ 435/74 |

FOREIGN PATENT DOCUMENTS

| | | |
|---|---|---|
| 0 559 249 A1 | 9/1993 | European Pat. Off. . |
| WO 94/20857 | 9/1994 | WIPO . |

OTHER PUBLICATIONS

Vojdani et al., *Immunopharmacology and Immunotoxicology* 16:497–523 (1994).
Wolf et al., *FASEB* 7:1265–1268 (1993).
Kossovsky et al., *Journal of Applied Biomaterials* 6:153–160 (1995).
Cuéllar et al., *The Journal of Rheumatology* 22:236–240 (1995).
Dauber et al., "Experimental silicosis," *American Journal of Pathology* 101:595–607 (1980).
Kossovsky et al., "Surface dependent antigens identified by high binding avidity of serum antibodies in a subpopulation of patients with breast prostheses," *Journal of Applied Biomaterials* 4:281–288 (1993).
Lilla et al., "Long–term study of reactions to various silicone breast implants in rabbits," *Plast. & Reconstr. Surg.* 57:637–649 (1976).
Naim et al., "Immuno–logical adjuvancy of silicone–gel," *Immunological Investigations* 22:151–161 (1993).
Nalbandian et al., "Long–term silicone implant arthroplasty," *Journal of the American Medical Assn.* 250:1195–1200 (1983).
Nosanchuk, "Injected dimethylpolysiloxane fluid: A study of antibody and histologic response," *Plast. & Reconstr. Surg.* 42:562–566 (1968).
Picha et al., "Cellular response to silicone," *Plast. & Reconstr. Surg.* 87:490–500 (1991).
Tenenbaum et al., "Identification of a novel autoantigen recognized in silicone–associated connective tissue disease," *American College of Rheumatology* (1992).
Wolf et al., "Human immune response to polydimethylsiloxane (silicone): screening studies in a breast implant population," *The FASEB Journal* 7:1265–1268 (1993).
Tenenbaum et al., "Identification of a novel antigen recognized by silicone implant recipients," *Arthritis and Rheumatism* 36 (9 Suppl), Abstract S118 (1993).
Teuber et al., "Anti–collagen Autoantibodies are Found in Women with Silicone Breast Implants," *Journal of Autoimmunity* 6:367–377 (1993).
Kossovsky et al., "Silicone Breast Implant Pathology," *Arch. Pathol. Lab. Med.* 118:686–693 (1994).
Tenenbaum et al., "Diagnostic and Clinical Criteria Distinguishing Silicone Related Disorders from Classical Rheumatic Diseases," *Arthritis and Rheumatism* 38 (9 Suppl), Abstract 1030, p. S325 (1995).
Teuber et al., J. Allergy Clin. Immunol., Jan. 1993, p. 240, abstract 396 "Anti–collagen Antibodies are Present in Women with Silicone Breast Implants".

*Primary Examiner*—Lora M. Green
*Attorney, Agent, or Firm*—Arnold, White & Durkee

[57] ABSTRACT

The present invention provides for a method of detecting antipolymer antibodies, and a method for detecting silicone related disease, fibromyalgia, and chronic fatigue syndrome.

10 Claims, 1 Drawing Sheet

METHOD FOR DETECTING ANTIPOLYMER ANTIBODIES AND DIAGNOSING SILICONE RELATED DISEASE (SRD) FIBROMYALGIA AND CHRONIC FATIGUE SYNDROME (CFS)

CROSS REFERENCE

This application is a continuation-in-part of application Ser. No. 08/320,889, filed Oct. 5, 1994 now U.S. Pat. No. 5,620,859.

FIELD OF THE INVENTION

This invention relates to a method and a kit for detecting antipolymer antibodies, and more particularly, to a method for diagnosing silicone related disease (SRD) fibromyalsia, and chronic fatigue syndrome (CFS).

BACKGROUND OF THE INVENTION

Various immunoassay techniques typically used in characterizing autoimmune responses, which are known to be extremely sensitive and specific, were used to identify antipolymer antibodies in over 50% of tested individuals diagnosed with silicone related disease and over 80% of tested individuals diagnosed with fibromyalgia and chronic fatigue syndrome. The detection of antipolymer antibodies provide the first definitive evidence that silicone breast implants are capable of producing an immunological response that is diagnostically testable, and the first evidence that an immunological response to fibromyalgia and chronic fatigue can be tested by an objective method.

Immunoassay techniques and methods generally known to those skilled in the art for detecting human antibodies are described in *Antibodies: A Laboratory Manual* by Ed Harlow and David Lane (1988) Cold Spring Harbor Laboratory, Cold Spring Harbor, N.Y. generally including homogenous and heterogeneous assay configurations. Currently, no known method exists for detecting antipolymer antigens, or serum antibodies immunologically produced in response to SRD, fibromyalsia, or CFS.

Silicone polymers have, until recently, been considered biologically and immunologically inert, and for this reason are included as exterior coatings on components of most medical devices that are surgically implanted into humans. Some examples of silicone containing devices include, hip replacements, catheters, mandibular prostheses, and breast implants. It has been estimated that more than 2 million women in the United States have been recipients of silicone implants for augmentation, mammoplasty and breast reconstruction following cancer surgery.

As devices such as silicone breast implants have become more widely used, an increased concern that silicone may be neither biologically nor immunologically inert has arisen. Silicones are entirely synthetic polymers containing a repeating Si-O backbone with organic groups attached directly to the silicon atom through a carbon bond. Silicone can be formed into fluids, gels, or solids based on the degree of linear, branched and cross link subunits. The degree of cross-inking dictates the consistency of the resulting silicone which can vary from a clear gel to a white opaque elastomer. The cross link polymers form a loose intertwining matrix which retains the remaining silicone fluid. The lack of chemical integrity of this complex is suspected to permit "gel bleed" of silicone fluid slowly out of the matrix. Impurities such as catalysts, short linear polymers, and small cyclics can remain depending on the stringency of the purification technique employed.

Approximately 10% of patients who receive medical devices containing silicone polymers experience complications including inflammation, severe muscle pain or overt rheumatic (autoimmune) disease. Recently, silicone implants have been linked to multiple sclerosis like symptoms, particularly in patients whose implants have ruptured. A portion of the approximately 2 million women in the United States who have received silicone gel filled breast implants have complications such as infection, capsular contraction, leakage and rupture (Touchette 1992). Additionally, some breast implant recipients experience a syndrome characterized by symptoms which include fibromyalsia, sicca syndromes, lymphadenopathy, contracture, sclerdoactyly, alopecia, edema, telangiectasias, changes in pigmentation, recurrent fever, skin rash, and chronic fatigue (Brozena, et al., 1988; Seleznick, et al., 1991; Vasey, et al., 1991; Copeland, et al., 1993; Spiera and Kerr, 1993; Spiera, et al., 1994).

Individuals surgically implanted with various devices containing silicone may also develop arthritic and dermatologic conditions that present like autoimmune diseases, such as systemic sclerosis (scleroderma) or Sjögren's Syndrome (Brozena, et al., 1988; Vasey, et al., 1991; Spiera, et al., 1994). Studies implicating silicone containing medical devices and autoimmune diseases, however, have been met with considerable skepticism (Gabriel, et al., 1994).

Exposure to silicone breast implants can result in the manifestation of symptoms and complications that collectively are dissimilar from previously recognized or defined rheumatological diseases and therefore may be uniquely identifiable with the appropriate diagnostic tests. Nevertheless, the systemic nature and relatively non-specific symptoms of the disease, particularly undifferentiated rheumatic and SRD, often make the disease difficult to clinically diagnose and difficult to distinguish. An assay method which would enable the clinician to distinguish and discriminate between undifferentiated rheumatic diseases and SRD is highly desired, and does not now currently exist.

Surgical implants have benefits that extend from prolongation of life to cosmetic enhancement. Implants also have associated risks, and these known risks motivate some people to forego implants even though the benefit may outweigh the risk. Likewise, removal of existing implants may involve expense, pain, disfigurement, disability and death. A diagnostic test that would help implant candidate balance the benefit and the risk of her/his implant is badly needed, and does not currently exist.

The diagnosis of fibromyalgia and chronic fatigue syndrome are currently based on subjective clinical observations comparing the symptomology of a patient with the symptomology formulated by the American College of Rheumatology for fibromyalgia, and Centers for Disease Control and Prevention for Chronic Fatigue Syndrome. Currently no known objective laboratory test exist to identify fibromyalgia or chronic fatigue patients.

SUMMARY OF THE INVENTION

It is the principal object of the invention to provide a reliable method for detecting antipolymer antibodies. It is also a principal object of the invention to provide a method for diagnosing silicone related disease, fibromyalgia, and chronic fatigue syndrome, It is also a principal object of the invention to provide an objective test for identifying silicone related disease, fibromyalgia, and chronic fatigue syndrome, through the detection of antipolymer antibodies in the test sera.

An exemplary embodiment of the invention achieves one or more of the above objects in an method for detecting antipolymer antibodies, by a) providing a sample to be tested for an antipolymer antibody and b) combining a polymer selected from the group consisting of polyacrylamide, silicone, and collagen, with said sample for a time sufficient for an antipolymer antibody to react with said polymer, to form a complex. An indicator reagent is added to the material resulting from step b) to indicate the presence or absence of an antipolymer antibody in said sample.

In a preferred method, the step of binding said polymer to a solid phase is further included.

In a preferred method, the solid phase is chosen from a group comprising nitrocellulose membranes, polyvinylidene difluoride (PEDF) and nylon.

In a preferred method, the indicator reagent is a binding member that is specific for a human antibody and conjugated to a detectable label and combined with said sample and polymer for a time under condition sufficient to form a label ternary complex on said solid support.

A preferred method, further including the step of detecting the presence or absence of labeled ternary complex as an indication of the presence or absence of said antipolymer antibody in said sample.

According to one aspect of the invention, the above objects are realized in a method diagnosing silicone related disease, comprising the steps of: a) providing a sample to be tested for an antipolymer antibody; and b) combining a polymer antigen selected from the group consisting of polyacrylamide, silicone and collagen, with said sample for a time sufficient for an antipolymer antibody to react with said polymer antigen to form a complex; c) reacting an indicator reagent with the material resulting from step b) to indicate the presence or absence of an antipolymer antibody in said sample. Identifying the presence or absence of a reacted indicator reagent in the material resulting from step c); whereby, the presence of reacted indicator reagent identifies silicone related disease in an individual providing said sample, with a clinical diagnoses of SRD.

According to one aspect of the invention, the above objects are realized in a method of diagnosing fibromyalsia, comprising the steps of: a) providing a sample to be tested for an antipolymer antibody; and b) combining a polymer antigen selected from the group consisting of polyacrylamide, silicone and collagen, with said sample for a time sufficient for an antipolymer antibody to react with said polymer antigen to form a complex; c) reacting an indicator reagent with the material resulting from step b) to indicate the presence or absence of an antipolymer antibody in said sample. Identifying the presence or absence of a reacted indicator reagent in the material resulting from step c), whereby, the presence of reacted indicator reagent identifies fibromyalsia in an individual providing said sample, with a clinic diagnoses of fibromyalsia.

According to one aspect of the invention, the above objects are realized in a method of diagnosing chronic fatigue syndrome, comprising the steps of: a) providing a sample to be tested for an antipolymer antibody; b) combining a polymer antigen selected from the group consisting of polyacrylamide, silicone and collagen, with said sample for a time sufficient for an antipolymer antibody to react with said polymer antigen to form a complex; and c) reacting an indicator reagent with the material resulting from step b) to indicate the presence or absence of an antipolymer antibody in said sample. Identifying the presence or absence of a reacted indicator reagent in the material resulting from step c); whereby, the presence of reacted reagent identifies chronic fatigue syndrome in an individual providing said sample, with a clinical diagnosis of chronic fatigue syndrome.

Other objects and advantages will become apparent from the following specification taken in connection with the accompanying Tables and Figures.

BRIEF DESCRIPTION OF THE DRAWINGS

The following drawing forms part of the present specification and is included to further demonstrate certain aspects of the present invention. The invention may be better understood by reference to the drawing in combination with the detailed description of specific embodiments presented herein.

DETAILED DESCRIPTION OF THE PREFERRED EMBODIMENT

Figure 1:
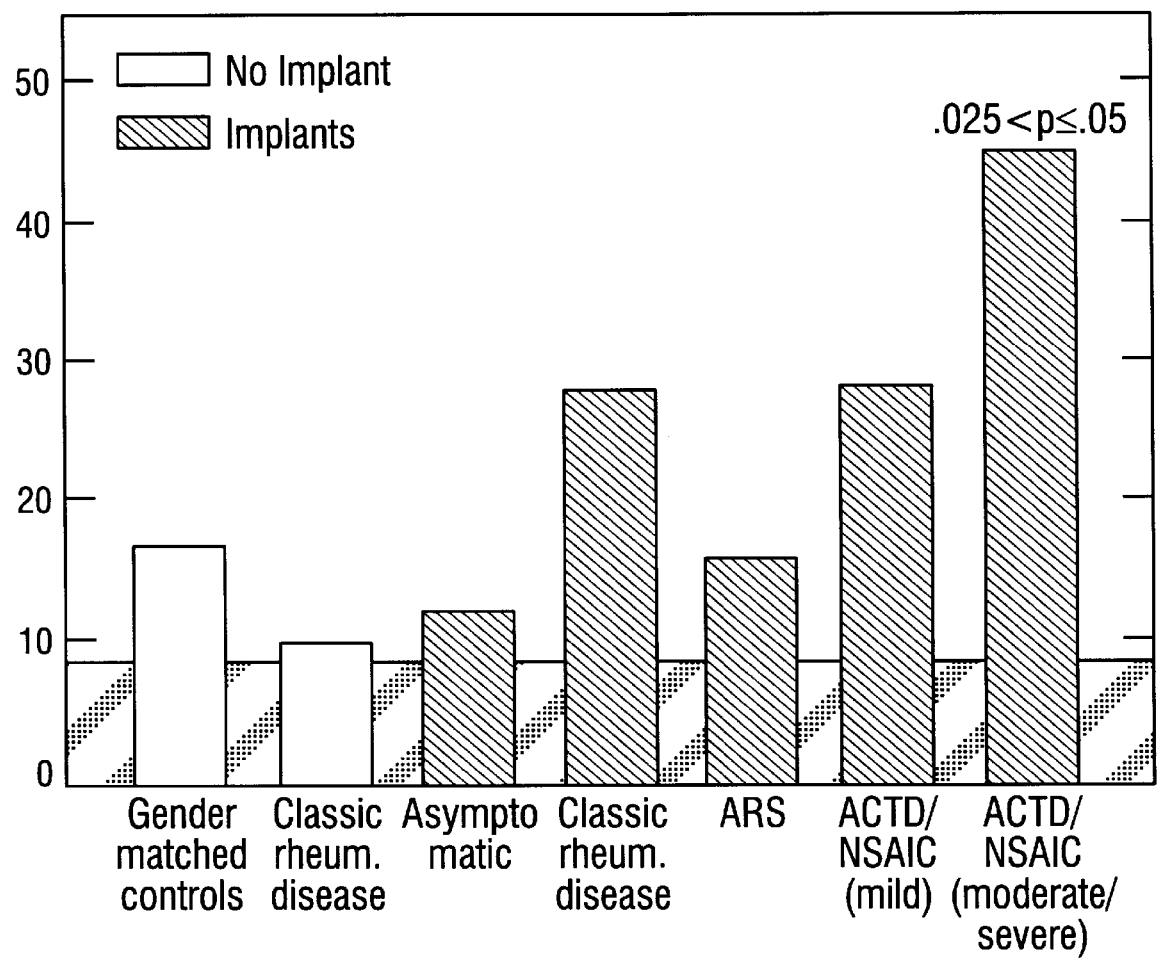
FIG. 1 shows the results of a blinded pilot study performed in Example 3 comparing sera of patients with and without implants.

The object of the present invention can be achieved by a variety of binding assay configurations and formats which enable the detection or measurement of polymer antigen and/or antipolymer antibodies (APA). Detailed herein, are presently preferred embodiments of the invention, in which it should be understood that the present disclosure is to be considered as an exemplification of the principals of this invention and is not intended to limit the invention to the embodiment described.

A method of detecting antipolymer antibodies includes the steps of providing a test sample of body fluid and mixing a polymer selected from the group comprising polyacrylamide, silicone or collagen with the sample for a time sufficient to form an antipolymer antibody and polymer complex, and combining an indicator reagent with the sample and polymer to detect the presence of antipolymer antibodies in said sample. The method can be used as a diagnostic tool in diagnosing patients with silicone related disease (SRD) fibromyalgia and chronic fatigue syndrome (CFS) of which no laboratory (objective) test currently exists to diagnose any of these three diseases.

A representative procedure for detecting antipolymer antibodies is an antipolymer antibody (APA) line blot analysis which is preferred and described in more detail hereinbelow. Alternatively, antipolymer antibodies, and the method for diagnosing SRD, fibromyalgia and CFS can be detected by other binding assays which are generally categorized into two major classes, namely, homogenous and heterogenous assays.

Homogenous assay configurations do not require the separation of the test solution and the indicator reagent prior to the detection of the indicator reagent or binding complexes. This broad classification includes many formats such as agglutination and precipitation assays as well as others known to those skilled in the art for the detection of antibodies and antigens.

Methods of the present invention can also be carried out using a solid phase sandwich assay (a heterogenous assay) to detect the presence or amount of antipolymer antibodies in the test sample. A capture reagent typically involving a specific binding member such as polymer antigen, or individual subunits thereof, is affixed to the solid phase material. A test sample is incubated with the capture reagent for a period of time under conditions sufficient for the formation of specific complexes between antipolymer antibodies in the test sample and the polymer antigen. The solid phase material can then be washed with a buffer solution including any buffer conventionally known to remove unbound test sample. The resultant complexes are then incubated with an indicator reagent, such as a second label polymer antigen, for a period of time and under condition sufficient for the formation of a ternary complex. The unreacted indicator reagent is removed by again washing the solid phase with a buffer solution. The quantity of indicator reagent bound to the solid phase is then measured by a technique compatible with the label component of the indicator reagent. If quantitated, the amount of indicator reagent bound to the solid phase is proportional to the quantity of test sample antipolymer antibody bound to the solid phase. The reagents of the method can be mixed simultaneously or added sequentially either singly or in combination.

In the present invention, the solid phase material can include any suitable chromatographic bibulous, porous or capillary material or other conventional solid material well known to those skilled in the art, used to immobilize specific binding members.

Specifically, the solid phase material can include a fiberglass, cellulose or nylon pad for use in a flow through assay devices having one or more layers containing one or more of the assay reagents; a dipstick for a dip and read assay; a test strip for chromatographic (i.e., paper or glass fiber) or thin layer chromatographic (i.e., nitrocellulose) techniques in which one or all of the reagents are contained in separate zones of a single strip of solid phase material; or an absorbent material well known to those skilled in the art. These solid phase materials can also include, without limitation, polyacrylamide beads, polystyrene beads or tubes, magnetic beads, a microtitre plate or a glass or plastic test tube.

Natural, synthetic, or naturally occurring materials that are synthetically modified, can also be used as a solid phase material including polysaccharides, i.e., cellulose materials such as paper, and cellulose derivatives such as diazobenzyloxymethylcellulose, nitrocellulose, 2-aminophenylthioetheylcellulose, and cellulose acetate; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (i.e., cotton) and synthetic (i.e. nylon); porous gels such as silica gel, agarose, dextran, and gelatin; polymeric films such as polyacrylates; protein binding membranes; and the like. The solid phase material should have reasonable strength or strength that can be provided by means of a support, and it should not interfere with the production of a detectable signal.

The capture reagent typically involves a specific binding member which has been bound to a solid phase material. The specific binding member can directly or indirectly bind the antibody, antigen or indicator reagent and which is bound or is capable of being bound to a solid phase or is capable of being precipitated such that the capture binding member can be separated from the test sample and other assay reagents by any means. The capture reagent of the present invention, is not limited to a capture binding member which is bound to an insoluble solid phase material. In an agglutination assay, the capture binding member of the capture reagent can be bound to a soluble carrier such as bovine serum albumin.

The specific binding member is a member of a specific binding pair, i.e., two different molecules wherein one of the molecules through chemical or physical means specifically binds (as opposed to nonspecific binding) to the second molecule. In addition to antigen and antibody, specific binding pairs, in which either one may be immobilized and bind to the test sample, may include: biotin and avidin; carbohydrates and lectins; complementary nucleotide sequences; complementary peptide sequences; effector and receptor molecules; enzyme cofactors and enzymes; enzyme inhibitors and enzymes; a peptide sequence and an antibody specific for the sequence or the entire protein; polymeric acids and bases; dyes and protein binders; protein A and antibodies; protein G and antibodies; and the like.

Furthermore, specific binding pairs can include members that are analogs of the original specific binding member, for example an analyte-analog. An analyte is defined as either the polymer antigen or the antipolymer antibody. If the specific binding member is an immunoreactant, it can be an antibody, antigen, hapten, or complex thereof. Further, antibodies can be monoclonal or polyclonal, a recombinant protein or antibody, a mixture(s) or fragment(s) thereof, as well as a mixture of an antibody and other specific binding members. The details of the preparation of such antibodies and their suitability for use as specific binding members are well known to those skilled in the art.

An indicator reagent comprises a detectable label directly or indirectly attached to a specific binding member which is capable of directly or indirectly binding to the antibody or antigen to indicate the presence or absence or amount of antibody or antigen. A variety of different indicator reagents can be formed by varying either the label or the specific binding member. In general the indicator reagent is detected after it has formed a complex with either the antibody or antigen or a complementary specific binding member, but the unbound indicator reagent can also be detected.

A label can refer to any substance which is attached to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including: colloidal metallic and nonmetallic particles, dye particles, enzymes or substrates, or organic polymer latex particles; liposomes or other vesicles containing signal producing substances (capable of reacting with another assay reagent, the antibody or antigen to produce a signal detectable by visual or instrumental means); and the like.

A method of the present invention can also be carried out using competitive assay formats. In a solid phase competitive assay, the capture reagent again typically involves a specific binding member which has been affixed to a solid phase material and which is contacted with both test sample and an indicator reagent. The indicator reagent, however, can be formed from an analyte or analyte-analog which has been conjugated with a label. A binding reaction occurs and results in the formation of complexes of (1) immobilized capture reagent/analyte complex and (2) immobilized capture reagent/indicator reagent complex. Alternatively, the immobilized specific binding member can be an analyte or analyte-analog with which the test sample analyte competes for binding to the indicator reagent. In the competitive assay, the amount of label on the solid phase is inversely related to the amount of analyte in the sample. Thus, a positive test sample will generally decrease in signal.

The preferred method for detecting the antipolymer antibody comprises an antipolymer antibody line blot analysis.

The partially polymerized acrylamide antigen is applied to a nitrocellulose support and cut into strips. The strips are incubated for one hour with a test sample, and an indicator reagent is then added to the strips thereby enabling the antipolymer antibody to be visualized.

The (APA) line blot analysis detects antipolymer antibodies in test sera with increased specificity and sensitivity over any other immunoassay. Antipolymer Antibodies are believed to specifically respond t the complex polymer PPA and can be identified over other nonspecific antisilicone antibodies utilizing the (APA) line blot analysis.

Additionally, the detection of Antipolymer Antibodies in test sera has been shown to correlate with SRD, fibromyalgia and CFS, three diseases that are believed to be associated in some way. This (APA) line blot analysis can be utilized to objectively detect an immunological response from SRD fibromyalgia, and CFS patients, identifying these patients from healthy blood donors and some other ill patients with well known autoimmune diseases.

In the present invention, the test sample can be obtained from any naturally occurring or artificially formed liquid test medium suspected of containing the antipolymer antibody, or polymer antigen. The test sample is generally a biological fluid or dilution thereof from which an antipolymer antibody or polymer antigen can be detected, including: serum; whole blood; plasma; body fluid; saliva; amniotic and cerebral spinal fluids; and the like.

In the present invention, the polymer antigen can be comprised of partially polymerized acrylamide, silicone, or collagen.

In addition to a nitrocellulose support, polyvinylidene difluoride (PVDF) and nylon can be alternative membrane sources. The (APA) line blot assay can also be adapted to a standard 96-well polystyrene enzyme linked immunosorbent assay (ELISA) format. Although the APA line blot was found to be the most preferred method, the APA line blot should be amenable to adaptation to other immunological assays including latex agglutination, antibody capture assays, radioimmunoprecipitation assays (RIPA), polystyrene bead based enzyme immunoassays (EIA), and particle concentration fluorescence immunoassays (PCFIA).

The antipolymer antibody line blot analysis typically involves the addition and incubation of several different reagents. A variety of different buffer and washing solutions can be used to stabilize the reagents and to remove excess reagents or test sample from the reaction. As is well known to those skilled in the art, modifications can be made in the buffer and washing solutions, as well as in the reaction times.

The assay reagents can also be provided in kit. A test kit to detect antipolymer antibodies would typically contain a support material upon which polymer antigen is immobilized and optionally include an appropriate supply of a suitable indicator reagent, buffer solutions and a suitable indicator reagent would comprise a binding member that is specific for human antibody, conjugated to a detectable label, and may include a calorimetric or chemiluminescent signal in the presence of an enzyme label.

A test kit to detect polymer antigen would typically contain a solid phase material upon which antipolymer antibody is immobilized or upon which components of the test sample can be immobilized (i.e., direct immobilization of the antigen upon the solid phase), and optionally include appropriate amounts of a suitable indicator reagent, buffer and washing solutions. Other components such as stabilizers and preservative agents can also be present in the kit and/or in the reagents.

Methods generally known to those skilled in the immunological arts are described in *Antibodies: A laboratory Manual* by Ed Harlow and David Lane, (1988), Cold Spring Harbor Laboratory, chapters 12 and 14 and are hereby incorporated by reference.

The following examples are given by way of representation and not limitation.

EXAMPLE 1

DETECTION OF ANTIPOLYMER ANTIBODY

Sample Collection

Serum from each subject or control were collected and stored at $-20°$ C. until shipment on ice by overnight carrier, and stored at $-20°$ C. or $4°$ C. until time of testing.

Anti-Polymer Antibody Line Blot Analysis

Partially polymerized acrylamide was prepared by mixing 2.5 ml Acryl:Bis (37.5:1), 8.5 ml $H_2O$ and 3.5 ml of 1.5M Tris. This 5% Acrylamide solution was cross-linked with 100 ml of 0.01% Ammonium per sulfate and 20 ml TEMED and allowed to solidify for 15 minutes in a 60 ml beaker. The PPA remains on top as a slight viscous liquid.

Aliquots of Polymer (PPA) were sequentially diluted 5, 25, 125, 625, and 3,125 fold, applied to nitrocellulose membranes and allowed to air dry. The nitrocellulose membranes was then cut into strips and incubated for one hour with blinded test sera diluted 1:400 in Western blot blocking buffer. Bound IgG or IgM were visualized by a series of reactions using biotinylated goat anti-human IgG or anti-human IgM avidin-conjugated horseradish peroxidase, and the enzyme substrates peroxide and 4-chloro-1-naphthol.

Each APA strip lot (28 strips) were run with a negative, weak-positive, and strong-positive control. The weak positive control served to standardize the enzymatic developing portion of the assay. Strip lots were standardized based on reactivity of control sera which subsequently were used to assess the level of reactivity of test sera.

EXAMPLE 2

COMPARISON OF PROCEDURES AND RESULTS

Frequency of Antipolymer Antibody in Unblinded Samples From Recipients of Silicone Breast Implants Detected By (APA) Line Immune Blotting Exposure to silicone breast implants can result in the manifestation of symptoms and complications that collectively are dissimilar from previously recognized or defined rheumatological diseases and therefore will be uniquely identifiable with the appropriate diagnostic tests. Using a combination of APA line blot techniques, it was determined that the approximately 50% (363/667) of persons reporting complications following silicone breast implantation produced APA serum antibodies. This was significantly greater than the 7% (7/100) observed in healthy blood donor sera ($p<0.0005$) (Table 1). Sera from patients experiencing other autoimmune complications (SLE, RA, juvenile rheumatoid arthritis, or diffuse scleroderma) demonstrated APA antibodies in less than 10% of the cases (Table 1). Therefore, antipolymer antibodies do not seem to be a general marker for autoimmunity. However, patients with the CREST form of scleroderma demonstrated detectable APA in 50% (10/20) of the cases tested. This is of interest because scleroderma-like symptoms, including tightness of skin, contracture, sclerodactyly, alopecia, edema, telangiectasias, rash, and change in pigmentation, have frequently been associated with silicone breast implants (Brozena et al., 1988; Vasey et al., 1991; Spiera et al., 1994).

Patients with complications associated with exposure to silicone from breast implants were 17 times more likely to produce detectable APA than healthy blood donors (95% confidence limit 7.55–46.69). This percentage is highly relevant to complications from breast implants because not all silicone breast implant recipients who are currently seeking treatment actually are experiencing complications directly resulting from silicone exposure.

Frequency of Antipolymer Antibodies In Unblinded Samples of 69 Patients with SRD To correlate the antipolymer antibody assay with the occurrence of specific clinical symptoms, sixty-nine patients with silicone disease as defined by joint aching about the MP's, PIP's, dysesthsias, paresthesias, multiple tender spots including the occiput, upper cervical, epicondyler, hips, knees and ankles, overwhelming fatigue, general malaise and widespread pain where studied. Of the 69 patients, 58 were felt to have silicone disease and 11 were felt to have no disease or localized myofascial discomfort.

Of the 69 patients, 5 patients had well-known rheumatic disease by American College of Rheumatology criteria, including 2 patients with primary Sjögren's syndrome, 1 patient with CREST, 1 patient with seropositive rheumatoid arthritis and 1 patient who met ACR criteria for lupus. There was 1 patient with chronic persistent hepatitis. Four patients had positive rheumatoid factors and 7 patients had antithyroid antibodies.

Fifty-eight patients had SRD; 11 patients had no disease.

Twenty-two patients had Antipolymer antibodies and SRD, thirteen patients had probable Antipolymer antibodies and SRD, totaling 35 patients with SRD having the presence of Antipolymer antibodies.

Sixty percent of the patients with SRD had the antipolymer antibody.

There were 11 patients without any silicone disease, and only 4 patients showed the presence of an Antipolymer antibody. This antibody is a very good predictor of SRD since 60% of patients with SRD had the antibody.

Frequency of Antinuclear Antibodies (Known Autoantigens) in Unblinded Samples of Patients With And Without SRD The antinuclear antibody test is routinely performed by rheumatologists for detecting scleroderma. The antinuclear antibody was present at low titer in 20° F. the 58 patients (34%) with SRD. The antinuclear antibody was present in 5 of the 11 patients (45%) without SRD, but myofacial pain. No correlation between the antinuclear antibody and SRD could be shown making the antinuclear antibody test not a good predictor of silicone disease.

Detection Of Antipolymer Antibody In An ELISA Format With A Sample Known To Be Positive For APA The following tables (tables 2, 3 & 4) demonstrate the detection of the antipolymer antibodies in an ELISA format. A dilution ratio of partially polymerized polyacrylamide antigen was attached to each well of a polystyrene 96-well plate as shown in column 1 of each table. The serum dilution ration (1/50, 1/100, etc.) for the representative patient sample is shown in the first row at the top of each column. The serum was incubated in the wells containing the antigen, then reacted with a goat-anti-human alkaline phosphatase labelled secondary antibody. The data was presented as an optical density from the signal production system from the reaction of this labelled secondary antibody with the substrate 5-bromo-4-chloro-3-indole phosphate (BCIP) phosphate. Wells containing neither PPA nor serum in the column marked blank are set to zero relative to the other wells. This test demonstrated the ability to test for antipolymer antibodies using the ELISA format.

TABLE 1

FREQUENCY OF ANTIPOLYMER ANTIBODIES IN UNBLINDED SAMPLES FROM RECIPIENTS OF SILICONE BREAST IMPLANTS, DETECTED BY (APA) LINE IMMUNOBLOTTING.

| Donor Groups/Diagnosis | # positive/ # tested | Percent Positive | Significance |
|---|---|---|---|
| healthy blood donors | 9/100 | 9.0% | |
| silicone implant recipients | 363/667 | 50.7% | $p<0.005$[a] |
| Scleroderma (CREST) | 10/20 | 50.0% | $p<0.005$ |
| Scleroderma (diffuse) | 1/10 | 10.0% | NSS[b] |
| systemic lupus erythematosus | 13/205 | 6.3% | NSS |
| adult rheumatoid arthritis | 3/92 | 3.3% | NSS |
| juvenile rheumatoid arthritis | 1/11 | 9% | NSS |

[a]student t test
[b]NSS = not statistically significant

TABLE 2

| PPA | Strong Positive | | | |
|---|---|---|---|---|
| dilution 1/50 | 1/100 | 1/200 | 1/400 | serum dilution |
| 0 | 0.392 | 0.068 | −0.042 | −0.09 |
| 1/15625 | 0.73 | 0.583 | 0.378 | 0.364 |
| 1/3125 | 2.013 | 2.5 | 2.038 | 1.587 |
| 1/625 | 2.5 | 2.5 | 2.5 | 2.5 |
| 1/125 | 2.5 | 2.5 | 2.5 | 2.047 |
| 1/25 | 2.5 | 2.5 | 2.5 | 2.5 |
| 1/5 | 2.5 | 2.5 | 2.5 | 1.373 |
| 1/ | 2.5 | 2.5 | 2.5 | 2.5 |

[0.392 is a background figure and clearly the antipolymer antibody was detected at all serum dilutions indicated by the number readings above the background reading.]

TABLE 3

| | Weak Positive | | | |
|---|---|---|---|---|
| 1/50 | 1/100 | 1/200 | 1/400 | serum dilution |
| 0 | 0.155 | 0.075 | −0.038 | −0.1 |
| 1/15625 | 0.435 | 0.18 | 0.105 | −0.08 |
| 1/3125 | 1.404 | 0.91 | 0.428 | 0.135 |
| 1/625 | 2.062 | 1.536 | 0.735 | 0.34 |
| 1/125 | 2.5 | 2.5 | 1.254 | 0.375 |
| 1/25 | 2.5 | 1.896 | 1.061 | 0.495 |
| 1/5 | 2.5 | 2.5 | 1.45 | 0.668 |
| 1/ | 2.5 | 2.5 | 2.5 | 1.379 |

TABLE 4

| | Negative | | | |
|---|---|---|---|---|
| 1/50 | 1/200 | 1/400 | blank | serum dilution |
| 0 | 0.117 | −0.062 | 0 | 0 |
| 1/15625 | 0.366 | −0.1 | 0.02 | 0 |

TABLE 4-continued

| | | Negative | | |
|---|---|---|---|---|
| 1/50 | 1/200 | 1/400 | blank | serum dilution |
| 1/3125 | 0.006 | −0.012 | 0.006 | 0 |
| 1/625 | 0.106 | −0.045 | 0.055 | −0.1 |
| 1/125 | 0.01 | −0.098 | 0.008 | −0.1 |
| 1/25 | 0.047 | −0.097 | −0.1 | 0.224 |
| 1/5 | −0.004 | −0.087 | 0.072 | −0.1 |
| 1/ | −0.039 | −0.1 | −0.1 | −0.1 |

EXAMPLE 3

THE DIAGNOSIS OF SILICONE RELATED DISEASE FROM THE DETECTION OF ANTIPOLYMER ANTIBODIES

The detection of APAs in this study may represent immunologic cross-reactivity directed against silicone or other components found in breast implants. Alternatively, silicone may function as an adjuvant and/or physically interact with cellular components present in the surrounding connective tissue, such as collagen. This may result in the structural alteration of the silicone or the cellular component so as to antigenically resemble partially polymerized acrylamide (PPA). Silicone, collagen, and PPA are all cross-linked polymers. It is possible that any antigenic relationship among these substances results from the type and degree of cross-linking, and not from chemical composition of the polymer.

The observation that exposure to silicone implants does not appear to be necessary for the development of APAs, is consistent with this latter hypothesis. About 7% of the healthy population appear to produce antibody that cross-react with PPA. This must be qualified because silicone containing devices are widely used in medicine, commerce, and industry, and it is possible that our normal blood donors may have been unknowingly exposed to silicone. Alternatively, individuals with preexisting APAs may be predisposed to complications following silicone implantation, although this has yet to be established.

Based on the observations with PPA and PPB (partially polymerized bisacrylamide—used to demonstrate that an antibody is indeed present) it is suspected that APAs react with a heterogeneous polymeric structure (possibly in a circular conformation) composed of acrylamide/bisacrylamide that may antigenically resemble a silicone implant polymer component. Although conjecture, a circular structure may provide the level of complexity necessary to convey antigenicity to a relatively simple polymer structure. Additionally, circular polymer complexes would be resistant to further polymerization and therefore, be more likely present as a partially polymerized component of an acrylamide gel.

To further demonstrate the ability of the APA test to identify patients with SRD, a blinded study was designed.

METHOD

Sera samples from individuals were obtained from a rheumatologist. Sample classifications were coded, and we were blinded to sample classification. Samples were then analyzed using the APA antibody test (line blot format) and results scored as to the presence or absence of antipolymer antibodies.

Samples from the following groups were included (See Table 5 and FIG. 1):

1) Gender and age matched healthy individuals; non-silicone implanted (23 samples)
2) Classic rheumatic disease; non-silicone implanted (19 samples)
3) Asymptomatic individuals; silicone implants (15 samples)
4) Atypical connective tissue disorders/nonspecific autoimmune complications (ACTD/NSAIC) mild and moderate/sever; silicone implanted (18 mild and 18 moderate/severe samples)
5) Atypical rheumatic syndrome (ARS);silicone implanted (43 samples)
6) Classical rheumatic disease; silicone implanted (18 samples)

Criteria for classification of sera samples

1) Systemic lupus erythematosus—A diagnosis of systemic lupus erythematosus was made in accordance to Tan EM, Cohen AS, Fries JF, et al: The 1982 revised criteria for the classification of systemic lupus erythematosus (SLE). Arthritis Rheum 25:1271–1277, 1982.
2) Progressive systemic sclerosis—A diagnosis of Progressive systemic sclerosis was made based on Masi AT, Rodnan GP, Medsger TA Jr, et al: Preliminary criteria for the classification of systemic sclerosis (scleroderma), Arthritis Rheum 23:581–590, 1980.
3) Mixed connective tissue disease/overlap syndrome—A diagnosis of mixed connective tissue disease required the presence of an RNP with negative SM and was based on the clinical description of this disease. Overlap syndrome required clinical symptoms with characteristics of two or more rheumatic diseases, specifically progressive systemic sclerosis, systemic lupus, myositis and rheumatoid arthritis.
4) Polymyositis or Dermatomyositis—A diagnosis of Polymyositis or Dermatomyositis was based on criteria by Bohan A, Peter JP, Bowman RL, et al: Computer-assisted analysis of 153 patients with polymyositis and dermatomyositis. Medicine (Baltimore) 56:255–286, 1977.
5) Sjögren's Syndrome—A diagnosis of Sjögren's Syndrome was made based on Fox RI, Robinson CA, Curd JC, et al: First international symposium on Sjögren's syndrome: Suggested criteria for classification. Scand, J. Rheumatol, 562:28, 1986.
6) Atypical connective tissue disease/Non-specific autoimmune condition-Patients with ACTD/NSAIC had a positive auto-antibody test and the presence of at least four of the following (a diagnosis of ACTD required a positive ANA result):
   a. Raynaud's phenomenon: patient gives a history of at least two color changes, visual evidence of vasospasm or digital ulcerations.
   b. Polyarthritis: defined as synovial swelling and tenderness in at least 3 or more joints, lasting greater than six weeks and observed by a physician.
   c. Arthralgia, in at least 3 or more joints.
   d. The subjective perception of xerophthalmia, and xerostomia.
   e. Myalgias; determined by objective tenderness upon physical examination.
   f. Rashes, including petechia, telangiectases, livedo reticularis, or erythematous vascular blotching.
   g. Pleuritis or pericarditis.
   h. Memory loss or difficulty concentrating with neuropsychological testing.

i. Peripheral neuropathy.
  j. Fatigue lasting at least six months.
  k. Lymphadenopathy.
  l. Photosensitivity: defined as the development of a rash on exposure to the sun.
  m. Dysphagia.
  n. Alopecia.
  o. Ataxia.
  p. Sleep disturbance.
  q. Easy bruisability or bleeding disorder.
  r. Chronic cystitis or bladder irritability.
  s. Irritable bowel syndrome or colitis.
  t. Fevers or night sweats.
  u. Mucosal ulcerations.
  v. Breast pain or sings/symptoms of encapsulation.
7. Autoantibodies:
  A. Positive ANA and RF (by nephelometry with 40 IU cutoff).
  B. Other autoantibodies such as Anti-DNA, SSA, SSB, RNP, SM, sci-70, centromere, Jo-1, PM-Scl, or dsDNA.
  C. Thyroid antibodies, anti-microsomal, or anti-cardiolipin.
  D. Other Serological Abnormalities:
    1. Elevation of immunoglobulin (IgG, IgA, IgM): or
    2. Serologic evidence of inflammation such as elevated ESR, CRP.
8. Atypical Rheumatic syndrome—A diagnosis of Atypical Rheumatic syndrome would be made when 5 of the above symptoms and/or findings were not accompanied by a positive autoantibody result.
9. Severity=severe ACTD/ARS or NSAIC requires at least breast pain with hardening of the breasts or encapsulation, or silicone granuloma on pathologic examination and rashes (i,e.: telangiectases, petechla). There is a decreased functional capacity consistent with the ability to perform only a few tasks of vocation, avocation and self-care.
10. Moderate=moderate ACTD/ARS requires that the patient have moderate pain or a functional capacity which allows the patient to perform some of the tasks of daily living.
11. Mild—mild ACTD/ARS patients are able to perform a majority of tasks required for daily living.

Results

As presented in Table 5 and FIG. 1, the APA test was able to uniquely identify patient sera from the ACTD/NSAIC category (SRD).

TABLE 5

Results from blinded study

| Subject Categories | Number of samples | APA Reactivity (%) | p-value |
|---|---|---|---|
| Non-Silicone Implanted | | | |
| Gender and age matched healthy individuals | 23 | 4(17%) | — |
| Classical rheumatic disease | 19 | 2(10%) | NSS |
| Systemic Sclerosis/Scleroderma | | | |
| Systemic Lupus Erythematosus | | | |
| Atypical Neurological Disease Syndrome | | | |
| Mixed Connective Tissue Disease/Overlap Syndrome | | | |
| Polymyositis/Dermatomyositis | | | |
| Primary Sjören's syndrome | | | |
| Silicone implanted | | | |
| Asymptomatic individuals | 15 | 2(13%) | NSS |
| Atypical connective issue disorders/Nonspecific autoimmune complications (ACTD/NSAIC) | | | |
| (mild) | 18 | 5(28%) | NSS |
| (Moderate/Severe) | 18 | 8(44%) | $.025 < p \leq .05$ |
| Atypical rheumatic syndrome (ARS) | 43 | 7(16%) | NSS |
| Classical rheumatic disease | 18 | 5(28%) | NSS |
| Systemic Sclerosis/Scleroderma | | | |
| Systemic Lupus Erythematosus | | | |
| Atypical Neurological Disease Syndrome | | | |
| Mixed Connective Tissue Disease/Overlap Syndrome | | | |
| Polymyositis/Dermatomyositis | | | |
| Primary Sjögren's syndrome | | | |

EXAMPLE 4

DIAGNOSIS OF FIBROMYALGIA FROM THE DETECTION OF ANTIPOLYMER ANTIBODIES

Diagnosis of fibromyalgia is currently based upon clinical observations as formulated by the American College of Rheumatology. As classified by the American College of Rheumatology in 1990, fibromyalgia is a syndrome characterized by chronic widespread pain in the absence of inflammation or muscle/skeletal abnormalities and pain in 11 of 18 tender points upon palpitation. Pain is often accompanied by the following symptoms: chronic fatigue; sleep disturbances, headache, and irritable bowel syndrome. (REF: Goldenberg, D. L. 1995. Fibromyalgia: why such controversy. Annals Rheumat.Dis. 54:3–5).

Except for pain upon digital palpitation of tender points, physical findings are frequently absent, and there is no known laboratory (objective) test that is diagnostic for fibromyalgia. It has been suggested that CFS and fibromyalgia may be identical conditions or at least have significant overlap, leading to misdiagnosis of one syndrome for the other. (REF: Buchwald, D., and Garrity, D. 1994. Comparison of patients with chronic fatigue syndrome, fibromyalgia, and multiple chemical sensitivities. Arch.Intern.Med. 154:2049–2053).

To demonstrate the ability to identify patients with fibromyalgia, the following blinded study was conducted.

Samples from patients and healthy individuals were assigned a unique number and submitted for analysis. Samples were analyzed for the presence of antipolymer antibodies using the APA line blot, without prior knowledge of the sample category. After analysis and tabulation of the data, the code correlating sample category with sample number was obtained and used to correlate results with sample category. Results indicating that the APA test is diagnostic for fibromyalgia is presented in Table 6.

TABLE 6

APA Results of CFS and Fibromyalgia

| | Sera Dilution | | |
|---|---|---|---|
| | 1:100 | 1:200 | 1:400 |
| Healthy Controls | 4/11 (36%) | 2/11 (18%) | 1/11 (9%) |
| Chronic Fatigue | 9/11 (82%) | 9/11 (82%) | 6/11 (55%) |
| Fibromyalgia | 14/17 (82%) | 12/17 (71%) | 12/17 (71%) |

As seen in the Sera Dilution of 1:400, when the healthy controls are reduced to below a 10% positive readings (95% confidence), antipolymer antibodies still appeared in 71% of patients with fibromyalgia.

EXAMPLE 5

DIAGNOSIS OF CHRONIC FATIGUE SYNDROME FROM THE DETECTION OF ANTIPOLYMER ANTIBODIES

Diagnosis of CFS is currently based on clinical observations of a minimum number of signs and symptoms as formulated by the Centers for Disease Control and Prevention.

Chronic Fatigue Syndrome (CFS) is characterized by debilitating fatigue (50% reduction in average daily activity) for a duration of six months or greater. It is typically accompanied by the following: mild fever; sore throat, unexplained muscle weakness; lymph node pain; myalgia; headaches; neurophysiological symptoms including excessive irritability; confusion; forgetfulness; and depression; sleep disturbances; and an acute or subacute onset of these symptoms. (ref: Calabrese, L. Danao, T. Camara, E. Wilke, W. 1992 Chronic Fatigue Syndrome. Amer.Fam.Phys. 45:1205–1213). Upon examination, Physical findings are frequently absent, and there is no known laboratory (objective) that is diagnostic for CFS (ref: Buchwald, D., and Garrity, D. 1994. Comparison of patients with chronic fatigue syndrome, fibromyalgia, and multiple chemical sensitivities. Arch.lntern.Med. 154:2049–2053).

To demonstrate the ability to identify patients with Chronic Fatigue Syndrome, the following blinded study was conducted.

Samples from patients and healthy individuals were assigned a unique number and submitted for analysis. Samples were analyzed for the presence of antipolymer antibodies using the APA line blot, without prior knowledge of the sample category. After analysis and tabulation of the data, the code correlating sample category with sample number was obtained and used to correlate results with sample category. Results indicating that the APA test is diagnostic for CFS is presented in Table 6 above.

As seen in Sera Dilution 1:400, when healthy controls are reduced to below 10% positive readings (95% confidence) antipolymer antibodies still appeared in over (55%) ½ the patients with CFS. At double the sera concentration, but with a slight decrease in accuracy, 82% of the patients with CFS tested positive for antipolymer antibodies.

We claim:

1. A method of detecting antipolymer antibody, comprising the steps of:
   a) providing a sample to be tested for an antipolymer antibody;
   b) combining partially polymerized acrylamide with said sample for a time sufficient for an antipolymer antibody to react with said polymer, to form a complex; and
   c) reacting an indicator reagent with the material resulting from step b) to indicate the presence or absence of an antipolymer antibody in said sample.

2. The method of detecting antipolymer antibody of claim 1 wherein said partially polymerized acrylamide is bound to a solid phase.

3. The method of detecting antipolymer antibody of claim 2 wherein the solid phase is chosen from a group comprising nitrocellulose membranes, polyvinylidene diflouride (PVDF), and nylon.

4. The method of detecting antipolymer antibody of claim 2 wherein said indicator reagent is a binding member that is specific for a human antibody and conjugated to a detectable label, and combined with said sample and partially polymerized acrylamide for a time and under conditions sufficient to form a labelled ternary complex on said solid support.

5. A diagnostic kit for use in detecting antipolymer antibody, comprising:
   a polymer antigen comprising partially polymerized acrylamide attached to a support material; and
   an indicator reagent comprising a binding member that is specific for human antibody and conjugated to a detectable label.

6. The diagnostic kit of claim 5 further comprising a wash composition for separating uncomplexed materials from an antipolymer antibody and polymer antigen complex.

7. The diagnostic kit of claim 5 wherein the indicator reagent is a colorimetric or chemiluminescent signal in the presence of an enzyme label.

8. A method to aid the diagnosis of silicone related disease (SRD) comprising the steps of:
   a) providing a sample to be tested for an antipolymer antibody;
   b) combining a polymer antigen comprising partially polymerized acrylamide with said sample for a time sufficient for an antipolymer antibody to react with said polymer antigen, to form a complex;
   c) reacting an indicator reagent with the material resulting from step b) to indicate the presence or absence of an antipolymer antibody in said sample; and
   d) identifying the presence or absence of reacted indicator reagent in the material resulting from step c);
   whereby the presence of reacted indicator reagent identifies silicone related disease in an individual providing said sample, with a clinical diagnosis of SRD.

9. A method to aid the diagnosis of fibromyalgia, comprising the steps of:
   a) providing a sample to be tested for an antipolymer antibody;
   b) combining a polymer antigen comprising partially polymerized acrylamide with said sample for a time sufficient for an antipolymer antibody to react with said polymer antigen, to form a complex;
   c) reacting an indicator reagent with the material resulting from step b) to indicate the presence or absence of an antipolymer antibody in said sample; and
   d) identifying the presence or absence of reacted indicator reagent in the material resulting from step c);
   whereby the presence of reacted indicator reagent identifies fibromyalgia in an individual providing said sample, with a clinical diagnosis of fibromyalgia.

10. A method to aid the diagnosis of chronic fatigue syndrome (CFS) comprising the steps of:
    a) providing a sample to be tested for an antipolymer antibody;

b) combining a polymer antigen comprising partially polymerized acrylamide with said sample for a time sufficient for an antipolymer antibody to react with said polymer antigen, to form a complex;

c) reacting an indicator reagent with the material resulting from step b), to indicate the presence or absence of an antipolymer antibody in said sample; and d) identifying the presence or absence of reacted indicator reagent in the material resulting from step c);

whereby the presence of reacted indicator reagent identifies CFS in an individual providing said sample, with a clinical diagnosis of chronic fatigue.

* * * * *